United States Patent [19]

Beck et al.

[11] Patent Number: 5,698,756
[45] Date of Patent: *Dec. 16, 1997

[54] TOLUENE ALKYLATION WITH ETHYLENE TO PRODUCE PARA-ETHYLOLUENE

[75] Inventors: Jeffrey S. Beck, Princeton, N.J.; Sharon B. McCullen, Newtown, Pa.; David H. Olson, Pennington; David L. Stern, Lawrenceville, both of N.J.

[73] Assignee: Mobil Oil Corporation, Fairfax, Va.

[*] Notice: The term of this patent shall not extend beyond the expiration date of Pat. No. 5,495,059.

[21] Appl. No.: 471,626

[22] Filed: Jun. 6, 1995

Related U.S. Application Data

[63] Continuation-in-part of Ser. No. 69,251, May 28, 1993, Pat. No. 5,476,823, and Ser. No. 338,297, Nov. 14, 1994, Pat. No. 5,495,059, which is a continuation of Ser. No. 69,255, May 28, 1993, Pat. No. 5,403,800.

[51] Int. Cl.$^6$ ................................................. C07C 2/68
[52] U.S. Cl. ............................................................ 585/467
[58] Field of Search ........................ 208/86, 257; 585/407, 585/418, 467, 475, 481, 533

[56] References Cited

U.S. PATENT DOCUMENTS

| | | |
|---|---|---|
| 3,251,897 | 5/1966 | Wise . |
| 3,257,310 | 6/1966 | Plank et al. . |
| 3,437,587 | 4/1969 | Elbert et al. . |
| 3,682,996 | 8/1972 | Kerr . |
| 3,698,157 | 10/1972 | Allen et al. . |
| 4,016,218 | 4/1977 | Haag et al. . |
| 4,049,738 | 9/1977 | Young . |
| 4,060,568 | 11/1977 | Rodewald . |
| 4,086,287 | 4/1978 | Kaeding et al. . |
| 4,090,981 | 5/1978 | Rodewald . |
| 4,100,215 | 7/1978 | Chen . |
| 4,117,024 | 9/1978 | Kaeding . |
| 4,127,616 | 11/1978 | Rodewald . |
| 4,145,315 | 3/1979 | Rodewald . |
| 4,224,141 | 9/1980 | Morrison et al. . |
| 4,283,306 | 8/1981 | Herkes ........................ 585/475 |
| 4,326,994 | 4/1982 | Haag et al. . |
| 4,402,867 | 9/1983 | Rodewald . |
| 4,443,554 | 4/1984 | Dessau . |
| 4,465,886 | 8/1984 | Rodewald . |
| 4,477,583 | 10/1984 | Rodewald . |
| 4,487,843 | 12/1984 | Telford et al. . |
| 4,522,929 | 6/1985 | Chester et al. . |
| 4,548,914 | 10/1985 | Chu . |
| 4,559,314 | 12/1985 | Shihabi . |
| 4,843,057 | 6/1989 | D'Amore et al. . |
| 4,851,604 | 7/1989 | Absil et al. . |
| 4,927,979 | 5/1990 | Yamagishi et al. ............. 568/791 |
| 4,950,835 | 8/1990 | Wang et al. . |
| 5,173,461 | 12/1992 | Absil et al. . |
| 5,321,183 | 6/1994 | Chang et al. ..................... 585/475 |
| 5,349,113 | 9/1994 | Chang et al. ..................... 585/475 |
| 5,349,114 | 9/1994 | Lago et al. ....................... 585/475 |
| 5,365,003 | 11/1994 | Chang et al. ..................... 585/470 |
| 5,367,099 | 11/1994 | Beck et al. ...................... 585/475 |
| 5,382,737 | 1/1995 | Beck et al. ...................... 585/475 |
| 5,403,800 | 4/1995 | Beck et al. ...................... 502/64 |
| 5,406,015 | 4/1995 | Beck et al. ...................... 585/475 |
| 5,455,213 | 10/1995 | Chang et al. ..................... 502/63 |
| 5,475,179 | 12/1995 | Chang et al. ..................... 585/475 |
| 5,476,823 | 12/1995 | Beck et al. ...................... 502/60 |
| 5,488,194 | 1/1996 | Beck et al. ...................... 585/475 |
| 5,495,059 | 2/1996 | Beck et al. ...................... 585/470 |
| 5,498,814 | 3/1996 | Chang et al. ..................... 585/475 |
| 5,516,736 | 5/1996 | Chang et al. ..................... 585/475 |
| 5,516,956 | 5/1996 | Abchandani et al. ............. 585/481 |
| 5,565,004 | 10/1996 | Beck et al. ...................... 585/475 |

FOREIGN PATENT DOCUMENTS 0 296 582 A2  6/1988  European Pat. Off. .

OTHER PUBLICATIONS

Nakajima et al., "p–Xylene–Selective Disproportionation of Toluene over a Modified Pentasil Type Zeolite", *Sekiyu Gakkaishi*, 35(2), 185–189 (1992).

Hibino et al., "Shape–Selectivity over HZSM–5 Modified by Chemical Vapor Deposition of Silicon Alkoxide", *Journal of Catalysis*, 128, 551–558 (1991).

Lago et al., "The Nature of the Catalytic Sites in HZSM–5 Activity Enhancement", *New Development in Zeolite Science Technology: Proceeding of the 7th International Zeolite Conference*, 677–684 (1986).

Primary Examiner—Michael Lewis
Assistant Examiner—Thomas G. Dunn, Jr.
Attorney, Agent, or Firm—Malcolm D. Keen; Peter W. Roberts

[57] ABSTRACT

There is provided a process for the alkylation of toluene with ethylene to selectively produce para-ethyltoluene over a catalyst which has been selectivated by multiple treatments with a siliceous material.

9 Claims, No Drawings

TOLUENE ALKYLATION WITH ETHYLENE TO PRODUCE PARA-ETHYLTOLUENE

CROSS-REFERENCE TO RELATED APPLICATIONS

This application is a continuation-in-part of U.S. application Ser. No. 08/069,251, filed May 28, 1993 now U.S. Pat. No. 5,476,828.

This application is also a continuation-in-part of U.S. application Ser. No. 08/338,297, filed Nov. 14, 1994, now U.S. Pat. No. 5,495,059, which is a continuation of U.S. application Ser. No. 08/069,255, filed May 28, 1993, now U.S. Pat. No. 5,403,800.

BACKGROUND

There is provided a process for the alkylation of toluene with ethylene to selectively produce para-ethyltoluene over a catalyst which has been selectivated by multiple treatments with a siliceous material.

Shape-selective catalysis is described, e.g., by N. Y. Chen, W. E. Garwood, and F. G. Dwyer, *Shape Selective Catalysis in Industrial Applications*, 36, Marcel Dekker, Inc. (1989). Within a zeolite pore, hydrocarbon conversion reactions such as isomerization, disproportionation, alkylation, and transalkylation of aromatics are governed by constraints imposed by the channel size. Reactant selectivity may occur when a fraction of the feedstock is too large to enter the zeolite pores to react, while product selectivity may occur when some of the products cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape-selective catalysis is demonstrated, for example, in selective alkyl-substituted benzene disproportionation to para-dialkyl-substituted benzene.

A representative para-dialkyl-substituted benzene is para-xylene. The production of para-xylene may be performed by methylation of toluene or by toluene disproportionation over a catalyst under conversion conditions. Examples include the reaction of toluene with methanol, as described by Chen et al., *J. Amer. Chem. Soc.*, 101, 6783 (1979), and toluene disproportionation, as described by Pines in *The Chemistry of Catalytic Hydrocarbon Conversions*, Academic Press, 72 (1981). Such methods may result in the production of a mixture of the three xylene isomers, i.e., para-xylene, ortho-xylene, and meta-xylene. Depending upon the degree of selectivity of the catalyst for para-xylene (para-selectivity) and the reaction conditions, different percentages of para-xylene are obtained. The yield, i.e., the amount of xylene produced as a proportion of the feedstock, is also affected by the catalyst and the reaction conditions.

Various methods are known in the art for increasing the para-selectivity of zeolite catalysts. One such method is to modify the catalyst by treatment with a "selectivating agent." For example, U.S. Pat. Nos. 5,173,461; 4,950,835; 4,927,979; 4,465,886; 4,477,583; 4,379,761; 4,145,315; 4,127,616; 4,100,215; 4,090,981; 4,060,568; and 3,698,157 disclose specific methods for contacting a catalyst with a selectivating agent containing silicon ("silicon compound").

U.S. Pat. No. 4,548,914 describes another modification method involving impregnating catalysts with oxides that are difficult to reduce, such as those of magnesium, calcium, and/or phosphorus, followed by treatment with water vapor to improve para-selectivity.

European Patent No. 296,582 describes the modification of aluminosilicate catalysts by impregnating such catalysts with phosphorus-containing compounds and further modifying these catalysts by incorporating metals such as manganese, cobalt, silicon and Group IIA elements. The patent also describes the modification of zeolites with silicon compounds.

U.S. Pat. No. 4,283,306 to Herkes discloses the promotion of crystalline silica catalyst by application of an amorphous silica such as ethylorthosilicate (i.e., tetraethylorthosilicate). The Herkes patent contrasts the performance of catalyst treated once with an ethylorthosilicate solution followed by calcination against the performance of catalyst treated twice with ethylorthosilicate and calcined after each treatment. The Herkes disclosure shows that the twice-treated catalyst is less active and less selective than the once-treated catalyst as measured by methylation of toluene by methanol, indicating that the multiple ex situ selectivation confers no benefit and in fact reduces a catalyst's efficacy in shape-selective reactions.

Steaming has also been used in the preparation of zeolite catalysts to modify the alpha or improve stability. For example, U.S. Pat. No. 4,559,314 describes steaming a zeolite/binder composite at 200°–500° C. for at least an hour to enhance activity by raising the alpha. U.S. Pat. No. 4,522,929 describes pre-steaming a fresh zeolite catalyst so that the alpha activity first rises then falls to the level of the fresh unsteamed catalyst, producing a stable catalyst which may be used in xylene isomerization. U.S. Pat. No. 4,443,554 describes steaming inactive zeolites (Na ZSM-5) to increase alpha activity. U.S. Pat. No. 4,487,843 describes contacting a zeolite with steam prior to loading with a Group IIIB metal.

Various organic compounds have been employed as carriers for silicon compounds in the silicon impregnation methods applied to zeolite catalysts. For example, U.S. Pat. Nos. 4,145,315; 4,127,616; 4,090,981; and 4,060,568 describe the use of inter alia $C_{5-7}$ alkanes as solvents for silicon impregnation.

SUMMARY

There is provided a process for alkylating toluene with ethylene, said process comprising contacting ethylene and toluene with a catalyst under sufficient alkylation conditions, wherein said catalyst comprises a zeolite and a siliceous material, wherein said catalyst is prepared by a method comprising the steps of:

(a) combining said zeolite with an organosilicon compound;

(b) calcining the organosilicon-containing material from step (a) in an oxygen-containing atmosphere under conditions sufficient to remove organic material therefrom and to deposit said siliceous material on the catalyst; and (c) repeating steps (a) and (b) at least once to deposit further siliceous material on said catalyst.

EMBODIMENTS

The parent zeolite, which is subjected to the selectivation treatment described herein, is preferably an intermediate pore size zeolite. Such intermediate pore size zeolites may have a Constraint Index of between about 1 and 12. A method for determining Constraint Index is described in U.S. Pat. No. 4,016,218. Examples of zeolites which have a Constraint Index from about 1 to 12 include ZSM-5, ZSM-11, ZSM-12, ZSM-22, ZSM-23, ZSM-35, ZSM-48, ZSM-50 and ZSM-57. An especially preferred zeolite is ZSM-5. Such zeolites are described, for example, in U.S. Pat. Nos. 3,702,886; Re. 29,949; 3,709,979; 3,832,449; 4,046,859; 4,556,447; 4,076,842; 4,016,245; 4,397,827; 4,640,849; 4,046,685; 4,175,114; 4,199,556; 4,341,7448; 3,308,069; and Re. No. 28,341.

Zeolites, such as ZSM-5, may be selectivated with a siliceous material by a vapor phase process or a liquid phase process. An example of a liquid phase selectivation process is described herein as a preselectivation or ex situ selectivation process. The preselectivation treatment involves depositing siliceous material on the catalyst by the steps of:

(a) combining a zeolite with an organosilicon compound; and
(b) calcining the organosilicon containing material in an oxygen containing atmosphere under conditions sufficient to remove organic material therefrom and leave the siliceous material on the zeolite.

In accordance with a selectivation procedure, termed herein as a multiple preselectivation procedure, these steps (a) and (b) are repeated at least once to provide multiple coatings of siliceous material on the catalyst.

Examples of multiple preselectivation techniques are provided in copending U.S. application Ser. Nos. 08/069,251; 08/069,254; 08/069,255; and 08/069,259, each filed May 28, 1993. Ser. No. 08/069,254 is now U.S. Pat. No. 5,367,099; Ser. No. 08/069,255 is now U.S. Pat. No. 5,404,800; and Ser. No. 08/069,259 is now U.S. Pat. No. 5,365,004. Ser. No. 08/069,251 is now U.S. Pat. No. 5,476,823.

The multiple preselectivation treatment may result in the deposition of at least 1 wt % of siliceous material on the catalyst.

A zeolite may be combined with a binder material for the zeolite. This binder material is preferably an inert, non-alumina binder material, such as a silica binder. A zeolite may be subjected to one or more selectivation treatments after the zeolite is combined with the binder material. Optionally, however, the zeolite may be selectivated in the unbound state.

Procedures for preparing silica bound zeolites, such as ZSM-5, are described in U.S. Pat. Nos. 4,582,815; 5,053,374; and 5,182,242. A particular procedure for binding ZSM-5 with a silica binder involves an extrusion process.

A particular process for preparing a silica-bound zeolite may comprise the steps of:

(a) mulling and then extruding a mixture comprising water, zeolite, colloidal silica and sodium ions under conditions sufficient to form an extrudate having an intermediate green strength sufficient to resist attrition during ion exchange step (b) set forth hereinafter;
(b) contacting the uncalcined extrudate of step (a) with an aqueous solution comprising ammonium cations under conditions sufficient to exchange cations in said zeolite with ammonium cations; and
(c) calcining the ammonium exchanged extrudate of step (b) under conditions sufficient to generate the hydrogen form of said zeolite and increase the crush strength of said extrudate.

In accordance with examples of a multiple preselectivation technique, the catalyst may be preselectivated by multiple treatments with a liquid organosilicon compound in a liquid carrier, each treatment being followed by calcination of the treated material in an oxygen containing atmosphere, e.g., air.

In accordance with the multiple impregnation preselectivation method, the zeolite is treated at least twice, e.g., from 3 to 6 times, with a liquid medium comprising a liquid carrier and at least one liquid organosilicon compound. The organosilicon compound may be present in the form of a solute dissolved in the liquid carrier or in the form of emulsified droplets in the liquid carrier. For the purposes of the present disclosure, it will be understood that a normally solid organosilicon compound will be considered to be a liquid (i.e., in the liquid state) when it is dissolved or emulsified in a liquid medium. The liquid carrier may be water, an organic liquid or a combination of water and an organic liquid. Particularly when the liquid medium comprises an emulsion of the organosilicon compound in water, the liquid medium may also comprise an emulsifying agent, such as a surfactant. Stable aqueous emulsions of organosilicon compounds (e.g., silicone oil) are described in copending U.S. application Ser. No. 08/141,758, filed Oct. 27, 1993. These emulsions are generated by mixing the organosilicon oil and an aqueous component in the presence of a surfactant or surfactant mixture. Useful surfactants include any of a large variety of surfactants, including ionic and non-ionic surfactants. Preferred surfactants include non-nitrogenous non-ionic surfactants such as alcohol, alkylphenol, and polyalkoxyalkanol derivatives, glycerol esters, polyoxyethylene esters, anhydrosorbitol esters, ethoxylated anhydrosorbitol esters, natural fats, oils, waxes and ethoxylated esters thereof, glycol esters, polyalkylene oxide block co-polymer surfactants, poly(oxyethylene-co-oxypropylene) non-ionic surfactants, and mixtures thereof. More preferred surfactants include surfactants having the formula α-[4-(1,1,3,3-tetramethylbutyl)phenyl]-ω-hydroxypoly(oxy-1,2-ethanediyl) (Octoxynols), most preferably octoxynol-9. Such preferred surfactants include the TRITON® X series, such as TRITON® X-100 and TRITON® X-305, available from Rohm & Haas Co., Philadelphia, Pa., and the Igepal CA series from GAF Corp., New York, N.Y. Emulsions formulated using such surfactants are effective for selectivating ZSM-5 to enhance shape selectivity, and to passivate surface acidity detrimental to product selectivity in certain regioselective catalytic applications such as the disproportionation of alkylbenzenes.

The organosilicon compound preselectivating agent may be, for example, a silicone, a siloxane, a silane or mixtures thereof. These organosilicon compounds may have at least 2 silicon atoms per molecule. These organosilicon compounds may be solids in pure form, provided that they are soluble or otherwise convertible to the liquid form upon combination with the liquid carrier medium. The molecular weight of the silicone, siloxane or silane compound employed as a preselectivating agent may be between about 80 and about 20,000, and preferably within the approximate range of 150 to 10,000. Representative preselectivation silicone compounds include dimethyl silicone, diethyl silicone, phenylmethyl silicone, methylhydrogen silicone, ethylhydrogen silicone, phenylhydrogen silicone, methylethyl silicone, phenylethyl-silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone, and ethylvinyl silicone. The preselectivating silicone, siloxane or silane compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used as preselectivating agents, as may silicones with other functional groups.

Preferred organosilicon preselectivating agents, particularly when the preselectivating agent is dissolved in an organic carrier or emulsified in an aqueous carrier, include dimethylphenylmethyl polysiloxane (e.g., Dow-550) and phenylmethyl polysiloxane (e.g., Dow-710). Dow-550 and Dow-710 are available from Dow Chemical Co., Midland, Mich.

When the organosilicon preselectivating agent is present in the form of a water soluble compound in an aqueous solution, the organosilicon may be substituted with one or more hydrophilic functional groups or moieties, which serve to promote the overall water solubility of the organosilicon compound. These hydrophilic functional groups may include one or more organoamine groups, such as —$N(CH_3)_3$, —$N(C_2H_5)_3$ and —$N(C_3H_7)_3$. A preferred water soluble organosilicon preselectivating agent is an n-propylamine silane, available as Hydrosil 2627 from Huls America.

When the zeolite is preselectivated by multiple impregnation techniques, the zeolite is calcined after each impregnation to remove the carrier and to convert the liquid organosilicon compound to a solid residue material thereof. This solid residue material is referred to herein as a siliceous solid material, insofar as this material is believed to be a polymeric species having a high content of silicon atoms in the various structures thereof. However, this siliceous solid residue material may also comprise carbon atoms in the structure thereof, resulting from the residue of the organo portion of the organosilicon compound used to impregnate the catalyst.

Following each impregnation, the zeolite may be calcined at a rate of from about 0.2° C./minute to about 5° C./minute to a temperature greater than 200° C., but below the temperature at which the crystallinity of the zeolite is adversely affected. This calcination temperature may be below 700° C., e.g., within the approximate range of 350° C. to 550° C. The duration of calcination at the calcination temperature may be from 1 to 24 hours, e.g., from 2 to 6 hours.

The impregnated zeolite may be calcined in an inert or oxidizing atmosphere. An example of such an inert atmosphere is a nitrogen, i.e., $N_2$, atmosphere. An example of an oxidizing atmosphere is an oxygen containing atmosphere, such as air. Calcination may take place initially in an inert, e.g., $N_2$, atmosphere, followed by calcination in an oxygen containing atmosphere, such as air or a mixture of air and $N_2$. Calcination should be performed in an atmosphere substantially free of water vapor to avoid undesirable uncontrolled steaming of the zeolite. The zeolite may be calcined once or more than once following each impregnation. The various calcinations following each impregnation need not be identical, but may vary with respect to the temperature, the rate of temperature rise, the atmosphere and the duration of calcination.

The amount of siliceous residue material which is deposited on the zeolite or bound zeolite is dependent upon a number of factors including the temperatures of the impregnation and calcination steps, the concentration of the organosilicon compound in the carrying medium, the degree to which the catalyst has been dried prior to contact with the organosilicon compound, the atmosphere used in the calcination and duration of the calcination.

Preferably, the kinetic diameter of the organosilicon compound, which is used to selectivate the zeolite, is larger than the zeolite pore diameter, in order to avoid entry of the organosilicon compound into the zeolite pores and any concomitant reduction in the internal activity of the zeolite.

Once the zeolite is preselectivated, it may, optionally, be further selectivated by a vapor phase selectivation technique. Vapor phase processes for selectivating zeolites are described in copending U.S. application Ser. Nos. 08/223,383, filed Feb. 25, 1993; 08/233,542, filed May 5, 1994; 08/306,567, filed Sep. 15, 1994; and 08/306,566, filed Sep. 15, 1994.

The present zeolite may be selectivated by more than one selectivation method, including those which are distinguished from the present selectivation method. In particular, for example, the zeolite may be partially selectivated with coke.

The activity and/or selectivity of the multiple preselectivated catalyst may be modified by exchanging ions thereon with alkali metal or alkaline earth metal ions. Methods for ion exchanging the multiple preselectivated catalyst with alkali metal ions (e.g., Na) are described in copending U.S. application Ser. No. (Attorney Docket No. 7669). Methods for ion exchanging the multiple preselectivated catalyst with alkaline earth metal ions (e.g., Mg) are described in U.S. application Ser. No. (Attorney Docket No. 7670). Generally, these methods involve the steps of:

(i) contacting the multiple preselectivated catalyst comprising a zeolite and siliceous material with an aqueous solution comprising at least one alkali metal or alkaline earth metal cation;

(ii) washing the aqueous solution-treated catalyst from step (i) with water;

(iii) drying the washed catalyst from step (ii); and (iv) recovering a catalyst composition comprising said zeolite, said siliceous material and alkali metal ions or alkaline earth metal ions from said aqueous solution of step (ii). Optionally, these ion exchange steps, particularly steps (i) and (ii), may be repeated at least once. Also, the dried, ion-exchanged catalyst may, optionally, be calcined, e.g., in pure nitrogen or air at a temperature from 200° F. to 1200° F., e.g., from 500° F. to 1000° F. The ion-exchanged versions of the present catalyst may comprise at least 0.03 wt. %, e.g., at least 0.1 wt. %, of alkali metal or alkaline earth metal. Particular alkali metals include Li, Na, K, Rb, and Cs. Particular alkaline earth metals include Mg, Ca, Sr, and Ba.

The selectivated zeolite is a catalyst. This catalyst may be used alone or in combination with other catalyst components included in catalysts of this type. Such other components include binders and hydrogenation/dehydrogenation components. Accordingly, it will be understood that the term, present catalyst, as used herein is intended to connote the presently selectivated zeolite in combination with other catalyst components, if any.

While not wishing to be bound by any theory, it is theorized that the extreme selectivity of the present catalyst is obtained by rendering acid sites on the external surfaces of the zeolite substantially inaccessible to reactants, while possibly increasing the tortuosity of the catalyst pore system. When a non-selectivated catalyst is used, it may be theorized that acid sites existing on the external surfaces of the zeolite isomerize the product para-isomer to the other two isomers, thereby reducing the amount of para-isomer in the product. By reducing the availability of these external acid sites to the product para-isomer, it is theorized that a relatively high proportion of the para-isomer can be retained. It is theorized that external zeolite acid sites are blocked or otherwise unavailable to the para-isomer in the present catalyst. The extreme para-selectivity of the present catalyst is especially surprising in the highly active forms of the catalyst.

The "alpha value" of a catalyst is an approximate indication of its catalytic cracking activity. The alpha test is described in U.S. Pat. No. 3,354,078 and in the *Journal of*

*Catalysis*, Vol. 4, 522–529 (1965); Vol. 6, 278 (1966); and Vol. 61, 395 (1980), each incorporated herein by reference to that description. It is noted that intrinsic rate constants for many acid-catalyzed reactions are proportional to the alpha value for a particular crystalline silicate catalyst (see "The Active Site of Acidic Aluminosilicate Catalysts," *Nature*, vol. 309, No. 5959, 589–591, (1984)). The experimental conditions of the alpha test preferably include a constant temperature of 538° C. and a variable flow rate as described in detail in the *Journal of Catalysis*, Vol. 61, 395 (1980). The present catalysts may have an alpha value less than 100, e.g., less than 50. In order to attain the desired degree of activity for the present catalyst, the alpha value of the multiple preselectivated catalyst may be reduced by at least 50%, e.g., at least 90%, by the above-mentioned ion-exchange procedure with alkaline earth metal or alkali metal, particularly sodium, ions.

The silica to alumina ratio of zeolites may be determined by conventional analysis. This ratio is meant to represent, as closely as possible, the ratio in the rigid atomic framework of the zeolite crystal and to exclude silicon or aluminum in the binder or in cationic or other form within the channels. The silica to alumina molar ratio of the ZSM-5 used to prepare the present catalysts may be, e.g., less than 200, e.g., less than 100, e.g., less than 60, e.g., less than 40, e.g., from about 20 to about 40. It will be appreciated that it may be extremely difficult to directly measure the silica to alumina ratio of zeolite after it has been combined with a binder material and selectivated by methods described hereinabove. Accordingly, the silica to alumina ratio has been expressed hereinabove in terms of the silica to alumina ratio of the parent zeolite, i.e., the zeolite used to prepare the catalyst, as measured prior to the selectivation of the zeolite and prior to the combination of this zeolite with the other catalyst components.

The crystal size of the parent zeolites of the present catalysts is preferably greater than 0.1 microns, as calculated by methods described hereinbelow. The accurate direct measurement of the crystal size of zeolite materials is frequently very difficult. Microscopy methods, such as SEM and TEM, may be used, but these methods require measurements of a large number of crystals and, for each crystal measured, values may be evaluated in up to three dimensions. Furthermore, in order to more completely characterize the crystal size of a batch of crystals, one should calculate the average crystal size, as well as the degree of variance from this average in terms of a crystal size distribution. Rather than relying upon such complex evaluations, crystal size is expressed herein in terms of a calculated value of average crystal size obtained by measuring the rate of sorption of 2,2-dimethylbutane at 90° C. and 60 torr hydrocarbon pressure. The crystal size is computed by applying the diffusion equation given by J. Crank, *The Mathematics of Diffusion*, Clarendon Press, 52–56 (1957), for the rate of sorbate uptake by a solid whose diffusion properties can be approximated by a plane sheet model. In addition, the diffusion constant of 2,2-dimethylbutane, D, under these conditions, is taken to be $1.5 \times 10^{-14}$ cm$^2$/sec. The relation between crystal size measured in microns, d, and diffusion time measured in minutes, $t_{0.3}$, the time required for the uptake of 30% capacity of hydrocarbon, is:

$$d = 0.0704 \times t_{0.3}^{1/2}.$$

Particular measurements expressed herein were made on a computer controlled, thermogravimetric electrobalance, but there are numerous ways one skilled in the art could obtain the data. Examples of larger crystal material have a sorption time, $t_{0.3}$, of 497 minutes, which gives a calculated crystal size of 1.6 microns. Examples of smaller crystal material have a sorption time of 7.8 minutes, and a calculated size of 0.20 microns.

As pointed out in the aforementioned U.S. Pat. No. 4,117,026, larger crystal size zeolites tend to have a greater intrinsic para-selectivity than smaller crystal size zeolites. It is theorized that this difference is attributable to the smaller ratio of external surface area to available internal surface area for larger zeolites as compared to smaller crystal size zeolites. Since it would theoretically require less selectivation to neutralize the external surface area of the more intrinsically para-selective larger crystal size zeolites, larger crystal size zeolites would be preferred to smaller crystal size zeolites, provided that all other factors were equal. However, there are other factors which tend to mitigate against a preference for larger crystal size zeolites, particularly ZSM-5. More particularly, larger crystal size ZSM-5 tends to be considerably more difficult to prepare than smaller crystal size ZSM-5, especially on a commercial scale. A particularly surprising aspect of the present siliceous material selectivated catalysts is that the zeolites thereof may comprise relatively small crystal size ZSM-5, e.g., having a crystal size of from about 0.1 to about 0.5 microns, and still have an extremely high degree of para-selectivity. When larger crystal size ZSM-5 is chosen for the present catalyst, this the crystal size of this ZSM-5 may be, for example, from about 1 to 2 microns.

The toluene feedstock for the present reaction may, optionally, include hydrocarbon impurities other than toluene. Such hydrocarbon impurities include non-aromatic hydrocarbons, such as paraffins and/or cycloparaffins. These non-aromatics may have boiling points close to the boiling point of toluene, which is about 111° C. These non-aromatics are, therefore, difficult to remove from toluene by distillation, and extraction techniques may be needed to separate these toluene coboilers from toluene. The amount of non-aromatics in the fresh feed may be from 0 wt. % to about 3 wt. %, e.g., from about 0.2 wt. % to about 1.5 wt. %. It will also be understood that the present toluene alkylation reaction may be run by recycling unconverted toluene. The amount of recycled toluene in the feed to the reactor will vary on the amount of toluene conversion per pass. For example, this feed may comprise from about 50 wt. % to about 85 wt. % of recycled toluene. As a result, difficult to remove non-aromatic constituents (e.g., toluene coboilers) may build up in the recycle stream. These toluene coboilers may eventually comprise from about 2 wt. % to about 15 wt. % of the toluene recycle stream. Thus, the total liquid feed to the present alkylation reactor may comprise both fresh (i.e., make-up) toluene and recycled toluene, and this liquid feed may comprise from 0 wt. % to about 15 wt. % of non-aromatics other than ethylene.

Reaction conditions for alkylating toluene with ethylene are described in U.S. Pat. No. 4,086,287 to Kaeding et al. Conversion conditions may include a temperature of from about 250° C. to about 600° C., a pressure of 0.1 atmospheres to about 100 atmospheres, a molar ratio of toluene/ethylene of about 1:1 to about 10:1 and a weight hourly space velocity (WHSV) of 0.1 to 100.

The present catalyst may, optionally, include a binder material. The optional binder for the present catalyst is preferably an inert, non-alumina containing material, such as silica. However, the binder may also be selected from other materials which may be used exclusively or in combination with one another or with silica. Examples of such binder materials include alumina, zirconia, magnesia, titania, thoria and boria. These materials may be used in the form of dried inorganic oxide gels of gelatinous precipitates. Examples of clay binder materials include bentonite and kieselguhr. The relative proportion of zeolite to the binder material may be about 30 to about 90 percent by weight. The bound catalyst may be in the form of an extrudate, beads or fluidizable microspheres.

EXAMPLE 1

The base catalyst ACC4 was prepared via multiple selectivation of parent HZSM-5, $Si/Al_2=26:1$, with Dow-550 silicone polymer. A total of four selectivations were carried out, each attempting to add 7.8 wt. % polymer onto the catalyst. The 4× selectivated catalyst was then subjected to exchange with 1M $NaNO_3$ solution. Three exchanges were carried out with a ratio of 50 mL of solution to 1 gram of zeolite extrudate. To illustrate the effectiveness of the exchange, the alpha value decreased from 650 for ACC4 to 36 for the exchanged catalyst. After exchange, the zeolite was dried at ca. 200° C. and used in the catalytic evaluation shown below, wherein toluene is alkylated with ethylene to selectively produce para-ethyltoluene.

| Conditions | | |
|---|---|---|
| Temp, °F. | 842 | 842 |
| Pressure, psig | 100 | 100 |
| Feed | | |
| WHSV (1/H) Toluene Feed | 10 | 5 |
| WHSV (1/H) Ethylene | 0.376 | 0.376 |
| Toluene/Ethylene/$H_2$ (molar) | 8/1/5.1 | 4/1/5.1 |
| Products | | |
| $C_5^-$ | 1.1 | 2.3 |
| Benzene | 0.17 | 0.20 |
| Toluene | 92.09 | 84.55 |
| Ethylbenzene | 0.14 | 0.29 |
| Para-xylene | 0.29 | 0.43 |
| Para-ethyltoluene* | 6.11 | 11.80 |
| Other Heavies | 0.15 | 0.31 |

*Some baseline trace for meta-ethyltoluene (<1% based on total ethyltoluene isomers)

The above table illustrates that nearly isomerically pure para-ethyltoluene can be produced in this reaction.

What is claimed is:

1. A process for alkylating toluene with ethylene, said process comprising contacting ethylene and toluene with a catalyst under sufficient alkylation conditions, wherein said catalyst comprises a zeolite having a constraint index of from about 1 to 12 and a siliceous material, wherein said catalyst is prepared by a method comprising the steps of:

(a) combining said zeolite with an organosilicon compound, wherein said organosilicon compound is selected from the group consisting of silicones and silicone polymers;

(b) calcining the organosilicon-containing material from step (a) in an oxygen-containing atmosphere under conditions sufficient to remove organic material therefrom and to deposit said siliceous material on the catalyst; and (c) repeating steps (a) and (b) at least once to deposit further siliceous material on said catalyst.

2. A process according to claim 1, wherein ions in said catalyst of step (c) are ion exchanged with sodium ions.

3. A process according to claim 1, wherein said zeolite is ZSM-5.

4. A process according to claim 3, wherein said ZSM-5 has a silica to alumina molar ratio of 60 or less.

5. A process according to claim 1, wherein said catalyst comprises at least 1 wt % of said siliceous material selectivating agent.

6. A process according to claim 1, wherein said catalyst further comprises a binder material.

7. A process according to claim 6, wherein said binder material is silica.

8. A process according to claim 1, wherein the conversion conditions comprise a temperature of from about 250° C. to about 600° C., a pressure of about 0.1 atmosphere to about 100 atmospheres, a weight hourly space velocity of from about 0.1 $hr^{-1}$ to about 100 $hr^{-1}$, and a toluene/ethylene molar ratio of from about 1:1 to about 10:1.

9. A process according to claim 1, wherein ions in said catalyst of step (c) are ion exchanged with alkali metal or alkaline earth metal ions.

* * * * *